Figure 1:
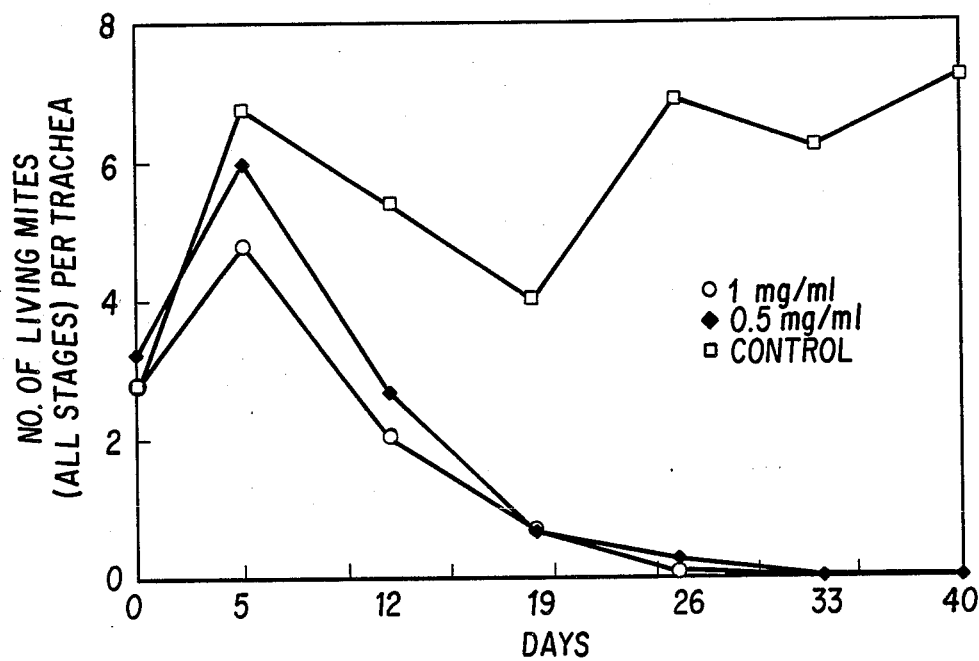

United States Patent [19]

Schmid

[11] Patent Number: 4,876,265

[45] Date of Patent: Oct. 24, 1989

[54] PROCESS AND COMPOSITIONS FOR CONTROLLING MITES PARASITIZING ON HONEY BEES

[75] Inventor: Wolfgang Schmid, Biel-Benken, Switzerland

[73] Assignee: Ciba-Geigy Corporation, Ardsley, N.Y.

[21] Appl. No.: 275,254

[22] Filed: Nov. 23, 1988

Related U.S. Application Data

[63] Continuation-in-part of Ser. No. 80,251, Jul. 27, 1987, abandoned, which is a continuation of Ser. No. 686,165, Dec. 24, 1984, abandoned, which is a continuation of Ser. No. 597,888, Apr. 9, 1984, abandoned.

[30] Foreign Application Priority Data

Apr. 14, 1983 [CH] Switzerland .......................... 2002/83

[51] Int. Cl.⁴ ............................................ A01N 43/78
[52] U.S. Cl. ..................................................... 514/370
[58] Field of Search ......................................... 514/370

[56] References Cited

U.S. PATENT DOCUMENTS 4,079,144  3/1978  Durr et al. ........................... 514/370

FOREIGN PATENT DOCUMENTS 2741457  8/1977  Fed. Rep. of Germany.
2139497  11/1984  United Kingdom ................ 514/370

OTHER PUBLICATIONS

The Illustrated Encyclopedia of Beekeeping, pp. 19–20. Differences in Biology and Means of Controlling Varroa Jacobsoni and Tropilaelap Clareae, two noval Parasitic Mites of Apismellifera.

Primary Examiner—Douglas W. Robinson
Assistant Examiner—Joseph A. Liporsky
Attorney, Agent, or Firm—Kevin T. Mansfield; Edward McC. Roberts

[57] ABSTRACT

A process for controlling parasitic honeybee mites, such as *Varroa jacobsoni*, *Acarapis woodi* and *Tropilaelaps clareae*, by the use of 2-(2,4-dimethylphenylimino)-3-methylthiazoline or an acid addition salt thereof, as well as novel compositions for controlling honeybee mites, which compositions contain these active ingredients. The active ingredients are administered in physiologically compatible preparations to the bees as feed or are applied in the beehive.

17 Claims, 1 Drawing Sheet

PROCESS AND COMPOSITIONS FOR CONTROLLING MITES PARASITIZING ON HONEY BEES

This application is a continuation-in-part of Ser. No. 080,251 filed 7/27/87, now abandoned; which is a continuation of Ser. No. 686,165 file 12/24/84, now abandoned; which is a continuation of Ser. No. 597,888 filed 4/09/84, now abandoned.

The present invention relates to a process for controlling honeybee mites by the use of 2-(2,4-dimethylphenylimino)-3-methylthiazoline or of an acid addition salt thereof, and to novel compositions for the control of honeybee mites, which compositions contain these substances as active ingredients.

Damage to bee colonies resulting from epidemic diseases caused by mites, such as *Varroa jacobsoni, Acarapis woodi* or *Tropilaelaps clareae* has become in the past few years a serious threat to bee stocks in many parts of the world, and has already led to considerable, economically serious losses occurring in honey yields. There has therefore been no shortage of attempts to find active substances and to develop methods for reducing the harm done to the honeybees by mites. A number of chemical substances have therefore already been tested with respect to their suitability for controlling honeybee mites (cf. N.Z.J. Exp. Agriculture 5, 2 (1977) 185–187). The methods which have hitherto become known for the control of honeybee parasites have, however, proved in practice to be not very satisfactory and inadequate to satisfy the demands made of them.

It has now been found that, surprisingly, the compound 2-(2,4-dimethylphenylimino)-3-methylthiazoline and salts thereof are suitable to a particularly high degree for successfully controlling mites which parasitize especially on bees, that is, on insects. It has also been established that these active ingredients are above all effective against the dangerous honeybee mites of the Varroa type, in particular against *Varroa jacobsoni*, the pathogen of the bee disease Varroatose.

FIG. 1 relates to the effect of 2-(2,4-dimethylphenylimino)-3-methylthiazoline on *Acarapis woodi* in package bee colonies.

By the acid addition salts of the compound 2-(2,4-dimethylphenylimino)-3-methylthiazoline used as active ingredients according to the invention are meant salts of suitable inorganic and organic acids. Examples are inorganic acids, such as: hydrofluoric acid, hydrochloric acid, hydrobromic acid or hydriodic acid, as well as sulfuric acid, sulfurous acid, phosphoric acid, phosphorous acid or nitric acid; and organic acids such as: acetic acid, trifluoroacetic acid, dichloroacetic acid, trichloroacetic acid, propionic acid, butyric acid, glycolic acid, thiocyanic acid, lactic acid, maleic acid, tartaric acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

The compound 2-(2,4-dimethylphenylimino)-3-methylthiazoline (=compound I) used according to the invention is a known compound which is described, as an acaricidal active substance, in the German Patent Specification No. 2,619,724, in the parallel British Patent Specification No. 1,527,807 and in the parallel U.S. Pat. No. 4,079,144. In the stated publications, there is described as the acaricidal property of this compound its effectiveness against the tick genera: Amblyomma, Rhipicephalus and Boophilus. These tick genera, however, are members of the order Acarina which as parasites live on and eat from mammals, for example cattle and sheep. It is therefore particularly surprising and was not foreseeable that the compound No. 1 used according to the present invention would be effective also against such mites, from among more than 30,000 known Acarina species, which are associated with an extremely different environment and biotope. There is namely not only the fact that honeybees, compared with the mammals already mentioned, constitute completely dissimilar host organisms, but also the fact that the preparation to be used must have a high tolerability for bees and at the same time no insecticidal properties, such as those occurring in parallel in the case of very many acaricides. It is surprising therefore that compound I exhibits precisely these essential properties of selectivity. Compound I and salts thereof are, however, particularly well suited for practical application also by virtue of their special biological properties. They exhibit a systemic action that renders possible their administration by way of the organs of the bee which effect the absorption of food and liquid, so that in this manner the said compounds, acting through the haemolymph of the bee, have a direct toxic effect on the sucking mites present. Furthermore, compound I and salts thereof are accepted by the bees as a feed additive and are thus not rejected, a property which was likewise not foreseeable. In virtue of the high tolerability of compound I for bees the concentration of the active ingredient in the feed and especially in feeding solutions is not critical at all. The process according to the invention hence brings about, by utilisation of the food circulatory system from bee to bee, in a very short time a high degree of distribution of the active substances, a condition which results in a rapid killing of all mites parasitizing on the bees and feeding on the haemolymph thereof. A contamination of the immediate environment of the bees with the administered active substance compound I is moreover improbable since the bees which have become healthy again do not empty their digestive tracts in the beehive.

In consequence of the favourable properties of the active substances (=compound I and salts thereof) and the special behaviour of the bees, very small amounts of the substances are sufficient to control the parasitic mites since these come into contact specifically with the active substances in the inventive process, a fact which is of great importance both from an economical and an ecological point of view.

The process according to the invention for controlling mites parasitising on honeybees comprises treating the bee colony threatened or infested by mite parasites with compound I or with an acid addition salt thereof. By 'threatened' here and in the following is also meant an already occurred mite infestation, which jeopardises the viability of the individual and the healthy development of the brood.

The treatment of the bees is effected by fumigating, spraying, atomising, dropping or feeding of the active substance. For this purpose, the active substances are formulated with suitable carriers and/or solvents. Suitable forms of administration of the compositions according to the invention are as follows:
*fumigant strips* containing, besides the active ingredient, for example potassium nitrate and cellulose;
*emulsifiable concentrates* consisting of the active ingredient and one or more suitable solvents tolerated by the bees, for example lower alkyl esters or triglycerides of natural or synthetic fatty acids, and suitable ionic or nonionic emulsifiers, such as nonylphenol polyglycol ether, alkylaryl polyglycol ether or phenyl sulfonate; and in some cases it is advantageous to use mixtures of various emulsifiers, as well as anti-foaming agents, for example silicones;

*concentrates dilutable with water,* consisting of the active ingredient and one or more solvents tolerated by the bees, for example water, dilute acids, ketones such as acetone, alcohols such as ethanol, glycols, polyethylene glycols or derivatives thereof and propylene glycol, as well as ethyl lactate, dimethylformamide, or similar solvents, which can additionally contain tensides; and

*wettable or dispersible and soluble powders consisting of the active ingredient and one or more carriers,* such as kaolin, talcum, precipitated silicic acid, bentonite, sodium, potassium-aluminium silicates, adipic acid, citric acid, sugar and sodium carbonate, as well as ionic or nonionic surface-active dispersing agents.

In the compositions according to the invention, the proportion of the active ingredient is 0.01 to 40 percent by weight, especially 0.1 to 8 percent by weight.

A particularly advantageous embodiment of the process according to the invention for controlling honeybee mites comprises the administration to the bees of the active substances or of compositions containing them by combining these with the food taken up by the bees (IN-FEED METHOD). For this purpose, nutrient solutions, for example sugar solutions, adapted to match the food of the bees and containing the active ingredients are fed to the bees as winter feed or in the manner of a stimulative feed. The palatability of the food to the bees is increased by the addition of attractants, preferably by citric acid.

As is known to those skilled in the art "the following (sugar) concentrations are mainly used (sugar:-water):1:4=20% for the stimulative feed in spring; 1:1=50%, the solution to be employed for early feed when the nectar flow stopped; 3:2=60%, this solution is a compromise between 1:1 and 2:1; 2:1=66.6%, only suitable for late feed" [Expression in brackets added] (Hüsing and Nitschmann (Eds.) Lexikon der Bienenkunde, 395, right column, Ehrenwirth, München, 1987).

Moreover, the combination of the active substance with the winter feed or the stimulative feed is especially advantageous because in times when this feed is offered normally no brood is present. At the beginning of winter time, the moment winter feed is offered to the bees, the population of the colony is about 20,000 bees. At the end of winter time, the moment the stimulative feed is offered to help the bees starting the brood rearing phase the population of the colony is reduced to about 10'000 bees [see Morse and Hopper, The Illustrated Encyclopedia of Beekeeping: Annual cycle of the colony, 19, Blandford Press, Poole, Dorset UK, (1985)].

A further advantageous method, which serves in particular to effect a very rapid absorption of the active substances by the bees, is the wetting of all of the bees or preferably of a part of the bee colony with the active substance solution (DRIP-ON METHOD). The wetting can be carried out by allowing the solution to drop onto the bees or by spraying. According to the specific nature of the behaviour of the bees, the wetted bees lick each other dry within several minutes so that the active substance passes quickly into the honey-sac and, by virtue of the metabolism or circulatory system of the bee colony, reaches within a short time all the bees. The wetting process can be carried out in a very practical manner by dropping the active substance solution from above onto a part of the bees present in the bee ways. It is not necessary to push the combs apart to do this, so that consequently the treatment proceeds very rapidly and without any appreciable disturbance of the bees. Also the fine dispersion of an active substance solution or emulsion within the bee colony using a microatomiser produces an excellent contact effect.

There are used for the treatment of a bee colony, depending on the form of application, concentrations of the active substance of 100 to 20,000 ppm (g/g), preferably 600 to 6,000 ppm (g/g). When active substance solutions are administered, the volume thereof per bee colony is in general 20 to 5,000 ml per treatment.

The application of the active substance within the beehive can in general be carried out as a preventive measure, that is to say, before a visible mite infestation exists. As a result of this measure, the haemolymph of the bees is enriched with traces of the active substance to such an extent that in the case of a mite infestation of individual bees acquired outside the beehive a multiplying of these parasites in the hive is prevented.

BIOLOGICAL EXAMPLES

Example 1: Feeding Method in the Laboratory

Thirty bees infested with varroa mites are each individually fed with 10 μl of a sugar-containing solution of 2-(2,4-dimethylphenylimino)-3-methylthiazoline. The active ingredient has been added as a 15% formulation to the sugar water prepared for the feed. After being fed, the bees are kept in groups each of 10 for 7 days in cages. The mites which in the course of the test have fallen off dead are collected in trays placed under the individual cages. The bees are subsequently killed and are examined for remaining mites. The counting of the mites that have fallen down and those remaining on the bees is carried out after 7 days.

| | Results | |
|---|---|---|
| Total mites | Fallen mites | Mortality rate in % |
| 35 | 34 | 97 |

The test result clearly shows the high effectiveness of the active ingredient killing nearly all of the parasitizing mites.

Example 2: Wetting method in the beehive

Six brood-less nuclei [small, manmade colonies of bees with usually 1000 to perhaps 5000 bees; see Morse and Hooper (1985), supra, Nucleus colony, p. 279] infested with varroa mites are treated three times, at intervals of 4 days, with a 0.5% aqueous solution of 2-(2,4-dimethylphenylimino)-3-methylthiazoline. The active substance is dissolved in the form of a concentrate formulation in water. 5 ml of the active substance solution are dropped onto a number of bees present in the bee ways of a beehive. The test is terminated 4 days after the last treatment, that is after a duration of 12 days. The mites and bees which have died in the course of the test are collected on a bottom tray covered with gauze, which has been inserted under the combs before commencement of the test. At the end of the test, the bees are killed, and the mites remaining on them are washed out in benzine and counted. For the evaluation, the number of dead mites and bees collected during the test is determined, the fact being taken into consideration that for the length of time of the test a natural mortality rate of about 0.5% of bees is to be expected.

| Results Killed organisms in % | |
|---|---|
| mites | bees |
| 91.8 | 0.4 |

The test result shows that the mortality of the bees during the test is exactly within the expected range and does not differ from the mortality of the untreated control group. This indicates the high tolerability and non-toxicity of the active ingredient for bees and on the other hand its high effectiveness with respect to the parasitizing mites.

Example 3: Tests under natural conditions 33 brood-less bee colonies (~20,000 bees) infested with varroa mites are divided into three groups and treated with 2-(2,4-dimethylphenylimino)-3-methyl-thiazoline in solutions of varying concentration, originating in one case from a 15% emulsion concentrate (EC-15) and in the other case from a 15% water-soluble powder (SP-15). In the latter case, the active ingredient I is in the form of a salt (cf. Formulation Examples).

All three groups A, B and C, each consisting of 11 colonies, receive during the time of treatment the same total amount of active ingredient.

In the following the applied amounts per bee way are given. Depending on the size of the bee colony, a bee-hive contains between 5 and 15 bee ways, so that the amount of active ingredient applied is correspondingly adjusted from hive to hive.

(A) 11 bee colonies-topical application

In each case 5 ml of a 4% aqueous solution or emulsion per bee way are sprayed onto a number of selected bees. The remaining bees provide for a uniform distribution of the active ingredient in the colony. The partial wetting procedure is repeated after 7 days and after 14 days (observation period 21 days).

(B) 11 bee colonies-oral long-term application

A 0.4% active-ingredient solution or emulsion in sugar water are offered to the bees for oral absorption, during 30 hours, in a feed bottle situated on the beehive. The amount of liquid in the container corresponds to 50 ml per bee way of the beehive concerned. This supply is repeated after 7 days and after 14 days (observation period 21 days).

(C) 11 bee colonies-continuous feeding 200 ml of a 0.3% active-ingredient solution or emulsion are offered to the bee colony, over a period of 14 days, from the feed container.

The mites and bees that have died during and after the treatment are collected daily from a bottom tray. 21 days after the first application, the bee colonies are killed and the remaining number of mites is then determined (observation period 21 days).

| Formulation | Form of application | Results mortality rate [%] (average values) | |
|---|---|---|---|
| | | mites | bees |
| | A-topical | 99 | 4 |
| EC-15 | B-oral | 98 | 0 |
| | C-oral | 96 | 1 |
| | A-topical | 99 | 0 |
| SP-15 | B-oral | 94 | 0 |
| | C-oral | 97 | 0 |

The test results demonstrate the high tolerability of the active ingredient for the bees and the high effectiveness for the mites. The mortality of the treated bees was exactly in the range of the untreated control group, namely in the range of about 1%.

As *Varroa jacobsoni*, the mite *Tropilaelaps clareae* parasitizes the honey bee *Apis mellifera* in Southeast Asia. A non-adapted host-parasite relationship can lead to significant losses of bees and colonies. Usually colonies are infested with both mites.

In experiments carried out in Thailand four different acaricidal acting products, 2-(2,4-dimethylphenylimino)-3-methylthiazoline, isoprpyl-4,4'-dibromobenzylate, 0,0-diethyl-0-(3-chloro-4-methylcoumarin-7-yl)-thiono-phosphonicacidester and "Illertissener Milbenplatte", a commercially available plate coated with a material releasing formic acid, were tested on 10 colonies each. Ten colonies were left as untreated controls.

In all treatments, dose rates proposed by the manufacturers for Varroa-mite-treatment were used in a comparative trial. Without optimising the dosage, the compound of the present invention resulted as the best product against both mites, *Varroa jacobsoni* and *Tropilaelaps clareae* (Ritter and Schneider-Ritter, in: Needham et al. (Eds.), Africanized Honey Bees And Bee Mites, Ellis Horwood Ltd., New York-Brisbane-Toronto, 1988, 387).

Example 4: *Acarapis woodi*

Forty-two packages of honey bees (2 lbs. ~907 g) are obtained from 22 colonies infested with *Acarapis woodi*. Infestations range from 60 to 100%. Each package is provided with a mated queen and 550 ml of treated or untreated 50% (wt/wt) sucrose syrup. All treated colonies receive syrup containing either 0.5 mg/ml (group B) or 1.0 mg/ml (group C) of 2-(2,4-dimethylphenylimino)-3-methyl-4-thiazoline hydrochloride. The control (group A) consists of 10 packages of bees and the treatment groups B and C of 16 packages each.

After installation on frames free of nectar and pollen, package colonies are examined at weekly intervals to determine food consumption, brood production and bee mortality. Random samples of ten bees/colony are examined on days 5, 12, 19, 26, 33 and 40. On day 0 and 5 bees are examined. Dissections and live mite determinations are made according to Eischen et al. (Am. Bee J. 127: 99–101, 1987).

There is a large increase in the number of mites of all stages during the 5-day holding, or customary shipping, period (see FIG. 1). The clustering of bees encountered during this period may facilitate an easy transfer and distribution of mites between the package bees because there are many young bees with numerous young female mites ready to lay eggs. Another possible explanation for the increase in the size of the mite population (see FIG. 1) is that the rate of success of dispersing females is very high because very few founding females are lost and thus unable to locate a new host under such crowded conditions.

Mite survival in groups B and C is less than 1 live mite/trachea after 14 days. After 26 days, no live mites are found in the tracheae of treated package bees. In the control, the highest infestation is recorded on day 40 (see FIG. 1).

Concentrations of 0.5 mg/ml and 1.0 mg/ml are detrimental to some honey bee larvae as spotty brood patterns are observed in several colonies. The effect is more pronounced at the higher concentration. Bees in treatment groups B and C utilize/hoard an average of 654 ml and 526 ml per colony, respectively, while bees in the control group (A) remove all of the 2000 ml of syrup offered.

The efficacy of the active compound is apparent after 7 days, and almost complete control of mites is recorded after 26 days. Relatively small amounts of the active compound appear to be necessary to control *Acarapis woodi*.

Exampe 5: *Acarapis woodi*

Three groups of honey-bee colonies (N=30) located in northeastern Mexico are selected on the basis of the prevalence of *Acarapis woodi* parasitizing their workers. Lightly (≦10%), moderately (20–60%), and heavily (90–100%) infested colonies are randomly assigned to control or treated subgroups (N=15). Controls receive 50% sucrose syrup, and treated colonies receive syrup medicated with 0.3 mg/ml 2-(2,4-dimethylphenylimino)-3-methyl-4-thiazoline-hydrochloride, small, medium, and large colonies receive 300, 600, and 1000 ml of syrup, respectively. Syrup is fed three times at weekly intervals.

At the end of treatment, the parasite load scores in medicated colonies are 0.53, 0.84, and 0.63 in the lightly, moderately, and heavily infested groups, respectively. This compared with 2.25, 3.43, and 1.13 parasite load scores of the control colonies of the same groups, respectively (P<0.05). In each group, some colonies do not respond typically to medication. High mite populations at the end of the test are associated with large colony size and large food reserves at the beginning of the test. Increased dosages, as well as redistribution/reduction of food reserves are recommended for greater efficacy.

Unexpectedly, medicated colonies have significantly larger bee populations than controls at the end of the test (P<0.05). Increased bee longevity due to parasite load reduction is suggested as the cause.

Example 6: Comparative test

Test compound according to the present patent application

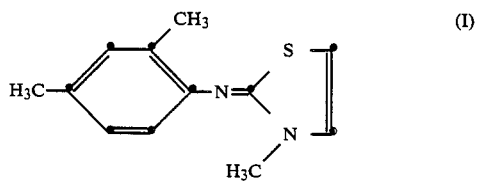

Comparative compounds according to U.S. Pat. No. 4,079,144

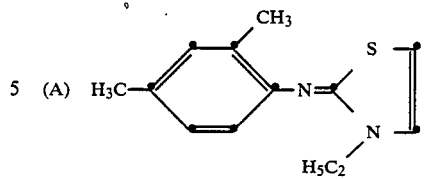

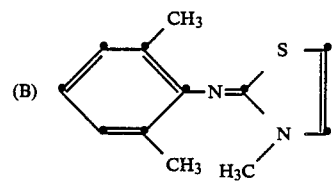

Compounds (I), (A) and (B) are formulated in accordance with Example F-1.

The age distribution of the bees in the test group is identical with that in a normal hive. The bees used in the laboratory tests originate from colonies only slightly infested with nosema. All groups of bees are infected with varroatosis (*Varroa jacobsoni*). To test the tolerance by the bees and the acaricidal activity in the group, 40 bees from the same colony are placed with their brood in each cage. To achieve a better control, each cage is fitted with a pane of glass. A small piece of honeycomb (6×8 cm) is attached at the top of each cage to pacify the bees. During the test period, the bees are kept in a climatic chamber at 25° C. and 85% relative humidity. These conditions are chosen because they are maximally acceptable both for the mites and the bees: the parasitizing mites are least affected and the bees live sufficiently long. To test the systemic activity of the active substance, 4 bees—within a group of 40 bees—are each individually fed with 10 μl of a suspension of the active substance in a 50% aqueous solution of sucrose. The bees have not been fed for at least one hour so that feed with a higher dose can be more readily ingested. 3 to 4 doses are tested in each of 2 groups. In each test series, 2 groups are left untreated as controls.

The behaviour of the bees reveal how well they tolerate the feed and how readily they ingest it. The bees are first observed in a small separate cage to establish whether or not they vomit the feed and only then they are put back to the rest of the group. After 24 and 48 hours, dead bees are counted and bee mortality is calculated.

24 and 48 hours after treatment, the activity on varroa mites is determined on the basis of mite mortality. For this purpose a tray (mesh width=2.4 mm) is fixed above the floor of each of the test cages. The mites which have dropped off the bees can thus be collected on paper which had been placed under the tray. 72 hours after treatment, the bees are sacrificed and then washed in benzine to determine the number of mites which have remained on them (method of determining the number of remaining mites according to Ritter, Apidologie, 1980, 11(2), 131–141).

Percentage mite mortality can be determined from the number of mites which have remained on the bees and the number which have dropped off. Using the Probit analysis (Cavalli-Sforza, Biometrie, G. Frischer Verlag, Stuttgart), the $LD_{50}$ can be determined from the dosage-mortality curve. The $LD_{50}$ relating to bees is not determined because the mortality of the bees in the presence of either of the three test compounds within the tested dosage range is smaller than 10% and, therefore, in the range of the control.

TABLE 1
Lethal dosage for varroa mites (*Varroa jacobsoni*)

| Time after application [hours] | [LD$_{50}$ in μg active ingredient/bee] | | |
|---|---|---|---|
| | Compound (I) | Compound (A) | Compound (B) |
| 24 | 17 | 35 | 28 |
| 48 | 13 | 35 | 28 |

In the described varroacidal test, compound (I) of the present patent application exhibits a significantly better activity against varroa mites than the homologous compounds (A) and (B) of the prior art. Effects on the test results by evaporation of the sugar solutions does not appear.

FORMULATION EXAMPLES

F-1: Emulsion concentrate (EC-15)
17.3 parts by vol. (=15.9 parts by wt.) of active ingredient,
10.9 parts by vol. of a 1:1:1 mixture consisting of:
 (a) a condensation product of 1 mol 4-isooctylphenol and 8.2 mol ethylene oxide,
 (b) ethoxylated castor oil,
 (c) phenyl sulfonate, and
71.8 parts by vol. of ethyl oleate
are thoroughly mixed to form 100 ml of emulsion concentrate which can be diluted to any extent with water and sprayed, or can be used as bee feed with for example portions of sugar.

F-2: Water-soluble powder (SP-15)
19.0 parts by wt. of active ingredient I (as hydrochloride or acetate)
1.0 part by wt. of highly dispersed pyrogenic silicic acid,
1.0 part by wt. of a condensation product of 1 mol 4-isooctylphenol and 8.2 mol ethylene oxide,
20.0 parts by wt. of adipic acid,
19.7 parts by wt. of powdered sugar, and
39.3 parts by wt. of normal sugar
are homogenised and form a readily water-soluble powder, which can be applied in the beehive or given as feed.

F-3: Active-ingredient concentrate
15 parts by wt. of active ingredient,
20 parts by wt. of lactic acid ethyl acetate, and
35 parts by wt. of distilled water
are well mixed to obtain a concentrate which can be diluted with water.

F-4: Active-ingredient concentrate
15 parts by wt. of active ingredient,
5 parts by wt. of nonylphenol polyglycol ether,
5 parts by wt. of alkaryl polyglycol ether,
5 parts by wt. of phenyl sulfonate, and
70 parts by wt. ethyl oleate
are well mixed to obtain an emulsifiable concentrate which can be diluted with water.

F-5: Dispersible powder
15 parts by wt. of active ingredient,
20 parts by wt. of adipic acid,
1 part by wt. of dispersed silicic acid,
0.5 part by wt. of nonylphenol polyglycol ether, and
63.5 parts by wt. of powdered sugar
are thoroughly mixed to obtain a powder dispersible in water.

F-6: Fumigant strip
400 parts by wt. of active ingredient and
143 parts by wt. of potassium nitrate
are melted and the melt is applied to 550 parts by weight of thick blotting paper. After the melt has cooled, the treated material is cut into strips. Such strips smoulder for 5-10 minutes, depending on the length, with the generation of smoke.

The chemical production of the active ingredient 2-(2,4-dimethylphenylimino)-3-methylthiazoline used in the process according to the invention and corresponding to the formula

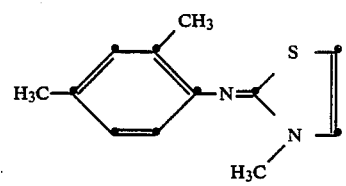

is known from the aforementioned literature (German Patent Specification No. 2,619,724; British Patent Specification No. 1,527,807; U.S. Pat. No. 4,079,144), and is effected by the reaction of N-(2,4-dimethylphenyl)-N'-methylthiourea with chloroacetaldehydediethylacetal.

I claim:
1. A process for controlling mites parasitizing on honeybees, which comprises administering a miticidally effective amount of 2-(2,4-dimethyphenylimino)-3-methylthiazoline or an acid addition salt thereof to said bees.

2. A process according to claim 1 wherein said administering is effected by fumigating, spraying, atomizing, dropping or feeding said compound to or on the bees.

3. A process according to claim 2 wherein said administering is effected by feeding said compound to the bees.

4. A process according to claim 3 wherein said administering is effected be feeding said compound in a sugar solution to the bees.

5. A process according to claim 1 wherein said compound is in the form of a hydrochloride salt.

6. A process according to claim 1 wherein said compound is administered in a composition containing the compound in a range of between 100 ppm and 20,000 ppm.

7. A process according to claim 6 wherein said range is between 600 ppm and 6000 ppm.

8. A process according to claim 1 wherein said compound is administered in a composition containing the compound in a range of between 0.01 and 40 percent by weight.

9. A process according to claim 8 wherein the composition contains the compound in a range of between 0.1 and 8 percent by weight.

10. A composition for controlling mites parasitizing on honeybees which contains a miticidally effective amount of 2-(2,4-dimethylphenylimino)-3-methylthiazoline or an acid addition salt thereof and sugar.

11. A composition according to claim 10 which further contains suitable carriers.

12. A composition according to claim 10 wherein said miticidally effective amount is in the range between 100 ppm and 20,000 ppm.

13. A composition according to claim 12 wherein said range is between 600 and 6000 ppm.

14. A composition according to claim 10 wherein said miticidally effective amount is in the range between 0.01 and 40 percent by weight.

15. A composition according to claim 14 wherein said range is between 0.1 and 8 percent by weight.

16. A process for controlling mites of the species *Varroa jacobsoni* parasitizing on honeybees which comprises administering a miticidally effective amount of 2-(2,4-dimethylphenylimino)-3-methylthiazoline or an addition salt thereof to said bees.

17. A process according to claim 16 wherein said administering is effected by feeding said compound in a sugar solution to the bees.

* * * * *